United States Patent [19]

Hanifin, Jr. et al.

[11] 4,254,049
[45] Mar. 3, 1981

[54] SUBSTITUTED PHENYL-2-CYANO-2-ALKENOIC ACID ESTERS

[75] Inventors: John W. Hanifin, Jr., Suffern; David N. Ridge, Upper Grandview, both of N.Y.

[73] Assignee: American Cyanamid Company, Stamford, Conn.

[21] Appl. No.: 104,510

[22] Filed: Dec. 17, 1979

[51] Int. Cl.³ .................. A61K 31/275; C07C 121/75
[52] U.S. Cl. .................... 260/465 D; 260/438.1; 424/304; 548/248
[58] Field of Search .............. 260/465 D, 438.1; 424/304

[56] References Cited

U.S. PATENT DOCUMENTS

| 4,061,767 | 12/1977 | Ertel et al. ............... 424/282 |
| 4,173,650 | 11/1979 | Hanifin, Jr. et al. ........... 424/304 |

Primary Examiner—Dolph H. Torrence
Attorney, Agent, or Firm—Edward A. Conroy, Jr.

[57] ABSTRACT

Substituted phenyl-2-cyano-2-alkenoic acid esters which are useful as anti-inflammatory agents and as inhibitors of the progressive joint deterioration characteristic of arthritic disease.

19 Claims, No Drawings

SUBSTITUTED PHENYL-2-CYANO-2-ALKENOIC ACID ESTERS

This invention is concerned with compounds of the formula:

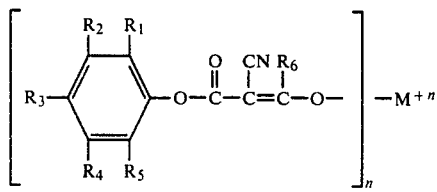

wherein $R_1$, $R_2$, $R_3$, $R_4$ and $R_5$ are each selected from the group comprising hydrogen, halogen, lower alkyl ($C_1$–$C_4$), lower alkoxy ($C_1$–$C_4$), trifluoromethyl and trichloromethyl; $R_6$ is lower alkyl ($C_1$–$C_4$); M is hydrogen or a pharmaceutically acceptable cation; and n is an integer 1, 2, or 3.

The useful pharmaceutically acceptable salts of the compounds of the above structural formula wherein M is hydrogen are those with pharmacologically acceptable metal cations, ammonium, amine cations or quaternary ammonium cations. Preferred metal cations are those derived from the alkali metals, e.g. lithium, sodium and potassium, and from the alkaline earth metals, e.g. magnesium and calcium, although cationic forms of other metals, e.g. aluminum, iron, zinc and in particular copper are within the scope of this invention.

Pharmacologically acceptable amine cations and those derived from primary, secondary or tertiary amines such as mono-, di- or trimethylamine, ethylamine, dibutylamine, triisopropylamine, N-methylhexylamine, decylamine, dodecylamine, allylamine, crotylamine, cyclopentylamine, dicyclohexylamine, mono- or dibenzylamine, α- or β-phenylethylamine, ethylenediamine, diethylenetriamine, and aryliphatic amines containing up to and including 18 carbon atmos, as well as heterocyclic amines, e.g. piperidine, morpholine, pyrrolidine, piperazine and lower alkyl derivatives thereof, e.g. 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g. mono-, di- or triethanolamine, ethyldiethanolamine, N-butylethanolamine, 2-amino-1-butanol, 2-amino-2-ethyl-1,3-propanediol, 2-amino-2-methyl-1-propanol, tris (hydroxymethyl)aminomethane, N-phenylethanolamine, N-(p-tert-amylphenyl)diethanolamine, galactamine, N-methylglucamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium and the like.

The compounds of the present invention may be prepared according to the following Flowchart A.

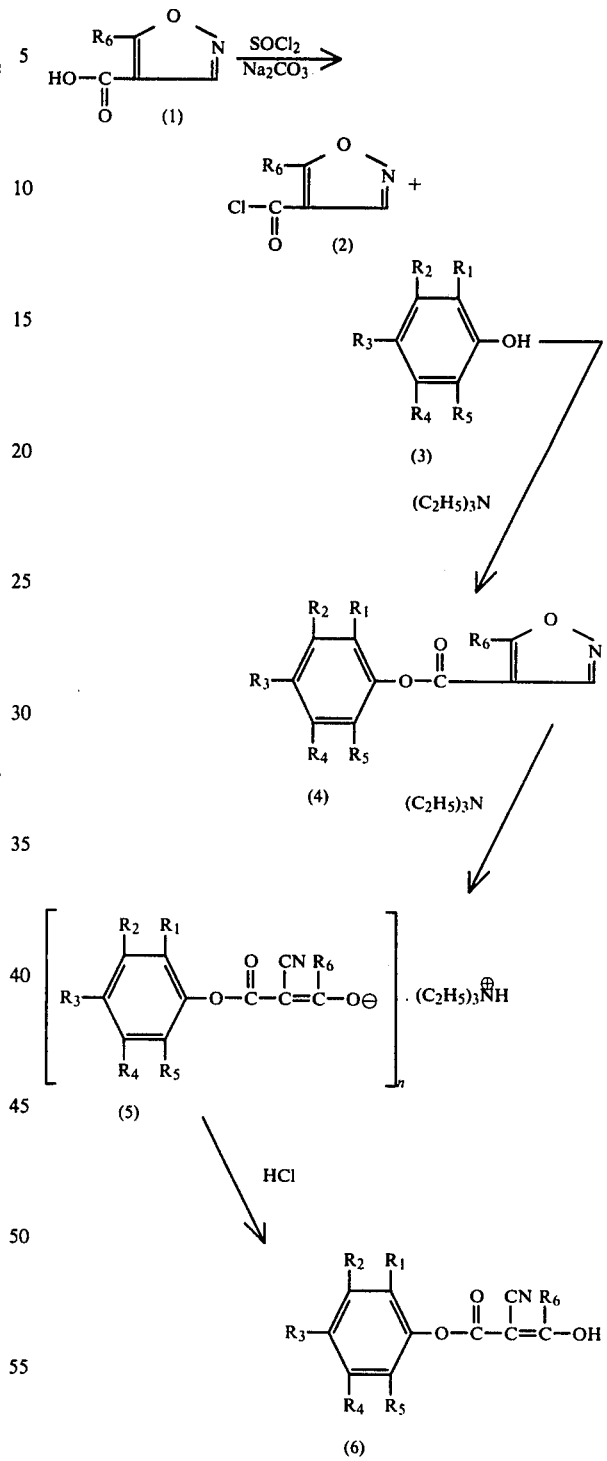

In accordance with Flowchart A, the 5-alkylisoxazole-4-carboxylic acid (1) [H. Yasuda, Yakugaku Zasshi, 79, 836–838 (1959); C.A., 53, 21885d] is reacted with thionyl chloride and sodium carbonate in chloroform with heat for several hours producing the corresponding 5-alkylisoxazole carbonyl chloride (2). The compound (2) is then reacted with the appropriate phenol (3) in ether at ice bath temperature with one molar equivalent of triethylamine for several hours giving the 5-alkyl-4-isoxazolecarboxylic acid phenyl ester (4). The ester (4) is treated with triethylamine at ice bath temperature for several hours giving the 2-cyano-3-substituted alkenoic acid phenyl ester triethylamine salt (5). The salt (5) is converted to the free ester (6) where $R_1$, $R_2$, $R_3$, $R_4$, $R_5$ and $R_6$ are as described above by treatment in aqueous solution with a mineral acid.

DETAILED DESCRIPTION OF THE INVENTION

The compounds of the present invention have been found to be highly useful for meliorating inflammation and inhibiting joint deterioration in mammals when administered in amounts ranging from about one milligram to about 250 mg. per kilogram of body weight per day. A preferred dosage regimen for optimum results would be from about 5 mg. to about 100 mg. per kilogram of body weight per day, and such dosage units are employed that a total of from about 0.35 gram to about 7.0 grams of the active ingredient for a subject of about 70 kg. of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the active ingredient may be administered in any convenient manner such as by the oral, intravenous, intramuscular, topical or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10 to 10.0% by weight, it is preferred that the amount of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, phenyl mercuric nitrate, benzalkonium chloride, phenethyl alcohol, p-chlorophenyl-α-glycerol ether, methyl and propyl parabens, and thimerosal. As a practical matter it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

For intramuscular injection, the preferred concentration of active compound is 0.25 to 0.50 mg./ml. of the finished compositions. The compounds of this invention are equally adapted to intravenous administration when diluted with water or diluents employed in intravenous therapy such as isotonic glucose in appropriate quantities. For intravenous use, initial concentrations down to about 0.05 to 0.25 mg./ml. of active compound are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active ingredient in such therapeutically useful compositions is such that a suitable dosage will be obtained. Preferred compositions or preparations according to the present invention are prepared so that an oral dosage unit form contains between about 50 and 250 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and popylparabens as preservatives, a dye and flavoring such as cherry or orange flavor. Of course, any material used in preparing any dosage unit form should be pharmaceutically pure and substantially nontoxic in the amounts employed.

The following test shows the activity of representative compounds of this invention against chronic inflammation in adjuvant induced arthritis which is accompanied by joint destruction. Groups of three Royal Hart, Wistar strain rats weighing 200±10 grams each were injected intradermally in the right hind paw with Freund's adjuvant (dried human tubercle bacilli in a mineral oil vehicle) at a dose of 2 mg./kg. of body weight. Test compound was administered orally in a 1.5% starch vehicle at various doses once daily on days 0 through 13 post challenge. Control rats were treated in a similar manner, but given only starch vehicle. On the 14th and 21st day post challenge the diameter of the injected paw (primary lesion) was measured by micrometer caliper. The volume of inflamed paws were estimated from these measurements and the results are expressed as percent inhibition of swelling as compared to controls. At the same time, the other inflamed sites, such as ears, paws and tail (secondary lesions) were observed and each rat was graded as to degree of inflammation and swelling present. The grading is based on a scale of 0 to 24, where 0 represents a complete absence of induced arthritic nodules and 24 represents the maximum degree of inflammation. The mean grade for each treated group is calculated and the effects of each compound are expressed as percent inhibition of the control grade. Table I records the results of tests conducted with typical compounds of the present invention. These compounds appear to suppress the progression of the arthritis and associated joint deterioration.

TABLE I

The Effect of Anti-inflammatory Agents on Adjuvant Induced Arthritis in Rats

| Compound | Oral Dose mg./kg. Body Weight | Dead/ Treated At 21 Days | Mean Weight Gain(grams) Day 14 | Mean Weight Gain(grams) Day 21 | % Inhibition of Swelling (Primary lesion) Day 14 | % Inhibition of Swelling (Primary lesion) Day 21 | % Inhibition of Control Grade (Secondary lesion) Day 14 | % Inhibition of Control Grade (Secondary lesion) Day 21 |
|---|---|---|---|---|---|---|---|---|
| 2-Cyano-3-hydroxycrotonic acid, p-chlorophenyl ester | 25 | 2/18 | 60 | 46 | 45* | 0 | — | — |
| 2-Cyano-3-hydroxycrotonic acid, 2,3-dichlorophenyl ester | 50 | 11/24 | 36 | 32 | 41* | 0 | — | — |
| 2-Cyano-3-hydroxycrotonic acid, o-chlorophenyl ester | 50 | 0/9 | 25 | 29 | 57* | 35 | — | — |
| Normal Rats (Historical) | — | 8/186 | 77 | 112 | — | — | — | — |
| Adjuvant Controls (Historical) | — | 53/630 | 36 | 31 | 0 | 0 | 0 | 0 |

*Significantly different from adjuvant controls.

Adjuvant induced experimental polyarthritis is a specific systemic disease of the rat which shares interesting similarities with rheumatoid arthritis. Specifically, the histology of the two diseases bears a remarkable resemblence as shown by C. M. Pearson, et al., Am. J. Path., 42, 73 (1963). E. M. Glenn, Am. J. Vet. Res., 27 (116), 339 (1966) has classified adjuvant induced polyarthritis as a crippling and permanent deformity resulting from diffuse connective tissue involvement around certain susceptible joints in the rat. Zahiri, et al., Can. Med. Ass. J., 101, 269 (1969) have shown that the fusiform swelling of the distal joints is associated with edema, congestion and synovitis including pannus formation, all of which precede the ultimate destruction of bone and cartilage. Furthermore, Zahiri, et al. indicate that the cartilage destruction in the joint is due to an invasive pannus which originates in the marginal synovium and extends across the articular surface to erode it. When non-steroidal, anti-inflammatory agents such as indomethacin inhibit arthritic paw swelling, which is composed of inflammatory cell infiltrates, they have also been shown to prevent joint and bone deterioration [see S. Wong, et al., J. Pharm. & Exp. Therm., 185, 127 (1973) and G. R. Bobalick, et al., Agents and Actions, 4, 364 (1974)]. The most pertinent reference showing the relationship betweem arthritis and joint deterioration is an X-ray analysis of adjuvant arthritis in the rat by Blackham, et al., Agents and Actions, 7, 145 (1977). In a similar manner, inhibition of the progress of arthritis in paws of rats treated with the compounds of this invention also lessens associated joint deterioration.

The compounds of the invention have been tested by the synovium-cartilage test which is a modification of the method described by Dumonde, D. C. and Glynn, L. E., The Production of Arthritis in Rabbits by an Immunological Reaction to Fibrin, Brit. J. Exp. Pathol., 43, 373 (1962).

Synovium-cartilage Test

Male, New Zealand rabbits, weighing 1.6–3.0 kg. were used. The rabbits were housed in individual cages and given food and water ad libitum. The rabbits were sensitized to bovine serum albumin (BSA) by injection of 20 mg./kg. BSA in complete Freund's adjuvant. The emulsion was injected subcutaneously into multiple sites on the back. Total injection volume equaled one mg./kg. of body weight. Between 18 and 21 days following immunization, the rabbits were challenged with an intraarticular injection of 5 mg. BSA into the right knee joint. Unanesthetized animals were restrained on their backs, and a 20-gauge, one-inch needle, with a 5 ml. syringe, was introduced into the joint and synovial fluid aspirated to determine that the synovium had been penetrated. The needle was then left in place for injection of the antigen. A 0.5 ml. portion of 10 mg./ml. BSA in sterile saline was injected into the synovial sac. The rabbits received an additional five intraarticular injections of 5 mg. BSA into the right knee at intervals of 12–16 days. Following the sixth injection the rabbits were sacrificed by an intracardiac injection of 5 ml. of a saturated solution of potassium chloride. The right knee was shaved. A longitudinal incision was made over the patellar ligament and the skin reflected under sterile conditions. The patellar ligament was cut transversely and reflected. Fascia and capsular tissue were trimmed from the lateral and medial aspects of the knee exposing the synovial membrane. The membrane was grasped with forceps, stretched laterally and then excised in a single piece on each side of the knee. The infrapatellar fat pad was removed and the joint space widened by cutting the anterior attachments of the menisci and severing the collateral cruciate ligaments. The femur and tibia were then separated and the menisci excised along with sufficient amounts of synovial tissue from the popliteal area adhering to the menisci. The tissues were immediately placed in a sterile Petri dish containing tissue culture medium composed of MEM ( Earle's salts) without sodium bicarbonate, with 25 mM Hepes buffer, pH adjusted to 7.34–7.37, and antibiotics (streptomycin and neomycin, 100 units/ml.). Ten percent normal rabbit serum (NRS) was added. The tissues were rinsed three times in fresh medium plus 10% NRS, then cut into pieces of 20–30 mg.

Articular cartilage was obtained from the knees of normal, young rabbits, weighing 1.0 to 1.5 kg. The knees were shaved, the rabbits sacrificed and the joint exposed as described above. Synovial tissue and the infrapatellar fat pad were removed. Ligaments were severed and the menisci excised. Femur and tibia were then separated and articular cartilage was cut from supracondylar lines, patellar surface and femoral condyles. Due to curvature of the bone, these pieces were not more than 6-7 mg. each. No cartilage was taken from the tibia. The cartilage was placed in a sterile Petri dish containing tissue culture medium plus 10% NRS and rinsed three times with fresh medium+10% NRS. The cartilage was then cut into 1-2 mg. pieces and stored at −70° C.

A 10 mg. portion of the test compound was dissolved or suspended in absolute ethanol. Ten µl. were then transferred to the complete tissue culture medium. The final concentration of test compound was then 10 mcg./ml. and the vehicle 0.1%.

Tissue culture medium was added to 12×75 mm clear plastic culture tubes containing one piece of normal articular cartilage. A piece of arthritic synovial tissue was then added to all tubes except those tubes in which cartilage was incubated alone. All tubes were then incubated at 37° C. for 48 hours with constant rotation in a roller drum at 0.2 rpm. After 48 hours the cartilage was removed, hydrolyzed and assayed for hexoseamine and hydroxyproline. Hexoseamine to hydroxyproline ratios were calculated for the three groups:

1. Cartilage alone
2. Cartilage+synovium
3. Cartilage+synovium+test compound.

Cartilage hexoseamine decreases when it is cultured in the presence of synovium but remains constant when cultured alone. Hydroxyproline remains constant in all groups and the amount assayed is a measure of the size of the incubated cartilage. Therefore, the hexoseamine/hydroxyproline ratio decreases in the cartilage+synovium group relative to the cartilage alone group. The decrease is approximately 50%.

If a compound prevents the decrease in the hexoseamine/hydroxyproline ratio by greater than 50% it is retested. A compound is considered active if it averages greater than 50% suppression of break down in three separate tests.

TABLE II

| Compound | No. of Tests | Mean % Inhibition |
|---|---|---|
| 2-Cyano-3-hydroxycrotonic acid, p-methoxyphenyl ester | 4 | 58.38 |
| 2-Cyano-3-hydroxycrotonic acid, p-tolyl ester | 3 | 50.34 |
| 2-Cyano-3-hydroxycrotonic acid, o-methoxyphenyl ester | 3 | 49.30 |
| 2-Cyano-3-hydroxycrotonic acid, o-fluorophenyl ester | 3 | 52.34 |

EXAMPLE 1

2-Cyano-3-hydroxycrotonic acid, p-chlorophenyl ester

A 130 ml. portion of thionyl chloride is added slowly to a mixture of 63.67 g. of 5-methylisoxazole-4-carboxylic acid [H. Yasuda, Yakugaku Zasshi, 79, 836-838 (1959); C.A., 53, 21885d] and 58.4 g. of sodium carbonate in 250 ml. of chloroform. The mixture is heated on a steam bath for 2 hours, filtered and the solvents are removed from the filtrate by evaporation. Two portions of chloroform are successively added to the residue and removed by evaporation. The resulting oil is distilled at 1-2 mm and the material boiling at 66°-68° C. is collected, giving 64.48 g. of 5-methylisoxazole carbonyl chloride.

A mixture of 12.86 g. of p-chlorophenol and 11.5 ml. (14.6 g.) of 5-methylisoxazole carbonyl chloride in 100 ml. of ether is cooled in an ice bath. A 14 ml. portion of triethylamine in 50 ml. of ether is added dropwise. The mixture is stirred for one hour and then filtered. The filtrate is evaporated to an oil which is distilled. The fraction boiling at 132°-137° C. is collected, giving 14.85 g. of 5-methyl-4-isoxazolecarboxylic acid, p-chlorophenyl ester.

An 8 ml. portion of triethylamine in 50 ml. of ether is cooled in an ice bath. A 10.15 g. portion of 5-methyl-4-isoxazolecarboxylic acid, p-chlorophenyl ester in 50 ml. of ether is added dropwise and then stirred overnight. The resulting solid is filtered and washed with ether, giving 12.41 g. of 2-cyano-3-hydroxycrotonic acid, p-chlorophenyl ester triethylamine salt as a white crystalline solid.

A 9.03 g. portion of the above salt is taken up in water, filtered and cooled. A 2.3 ml. portion of concentrated hydrochloric acid is added giving 6.33 g. of the desired product as crystals, mp. 97°-100° C.

EXAMPLE 2

2-Cyano-3-hydroxycrotonic acid, 2,3-dichlorophenyl ester

A 16.3 g. portion of 2,3-dichlorophenol and 11.15 ml. (14.6 g.) of 5-methylisoxazole carbonyl chloride in 50 ml. of ether is cooled in an ice bath and a solution of 14 ml. of triethylamine is added dropwise. The mixture is stirred for 3 hours and the solid is filtered and washed with ether. The combined filtrate and wash is evaporated to an oil on a steam bath. This oil is taken up in methylene chloride, filtered through diatomaceous earth and the filtrate evaporated on a steam bath with the addition of hexanes to about 50 ml. Cooling gives 24.02 g. of 5-methyl-4-isoxazolecarboxylic acid, 2,3-dichlorophenyl ester as a tan crystalline solid.

A 17.95 g. portion of the above isoxazole is slurried in 100 ml. of ether and cooled in an ice bath. A solution of 12 ml. of triethylamine in 50 ml. of ether is added dropwise and the reaction is stirred overnight. The solid is recovered by filtration and dried, giving 22.92 g. of 2-cyano-3-hydroxycrotonic acid, 2,3-dichlorophenyl ester, triethylamine salt as a light tan crystalline solid.

An 11.88 g. portion of the above salt is slurried in 100 ml. of water and acidified with 2.65 ml. of concentrated hydrochloric acid. The mixture is stirred for several hours and the solid is filtered and dried, giving 8.52 g. of the desired product, mp. 142°-146° C.

Following the general procedure of Examples 1 and 2 other representative compounds of this invention, such as those found in Table III, may be made.

TABLE III $$\underset{(1)}{\underset{HO-C}{\overset{O}{\|}}\underset{}{R_6}\overset{O}{\underset{N}{\diagdown}}} \longrightarrow \underset{(2)}{\underset{Cl-C}{\overset{O}{\|}}\underset{}{R_6}\overset{O}{\underset{N}{\diagdown}}} + \underset{(3)}{R_3\underset{R_4\ R_5}{\overset{R_2\ R_1}{\bigcirc}}-OH} \longrightarrow$$

$$\underset{(4)}{R_3\underset{R_4\ R_5}{\overset{R_2\ R_1}{\bigcirc}}-O-\underset{\|}{\overset{O}{C}}-\underset{}{R_6}\overset{O}{\underset{N}{\diagdown}}} \longrightarrow \underset{(5\ \&\ 6)}{\left[R_3\underset{R_4\ R_5}{\overset{R_2\ R_1}{\bigcirc}}-O-\underset{\|}{\overset{O}{C}}-\underset{}{\overset{CN}{C}}=\underset{}{\overset{R_6}{C}}-O-\right]_n M^{+n}}$$

| Example | Alkylis- oxazole Acid (1) $R_6 =$ | Alkylis- oxazole Chloride (2) $R_6 =$ | Phenol (3) | Alkylis- oxazole carboxylic Phenyl Ester (4) | 2-Cyano Alke- noic Acid Phenyl Ester Triethylamine Salt (5) | 2-Cyano Alkenoic Acid Phenyl Ester (6) | M.P. °C. | Method of |
|---|---|---|---|---|---|---|---|---|
| 3 | $CH_3$ | $CH_3$ | $R_1$-$R_4$ = H $R_5$ = Cl | $R_1$-$R_4$ = H $R_5$ = Cl | M = $(C_2H_5)_3$N $R_1$-$R_4$ = H $R_5$ = Cl | M = H $R_1$-$R_4$ = H $R_5$ = Cl | 88–92 | Example 1 |
| 4 | $CH_3$ | $CH_3$ | $R_1$, $R_2$, $R_4$, $R_5$ = H $R_3$ = $CH_3O$ | $R_1$, $R_2$, $R_4$, $R_5$ = H $R_3$ = $CH_3O$ | M = $(C_2H_5)_3$N $R_1$, $R_2$, $R_4$, $R_5$ = H $R_3$ = $CH_3O$ | M = H $R_1$, $R_2$, $R_4$, $R_5$ = H $R_3$ = $CH_3O$ | 112–115 | Example 2 |
| 5 | $CH_3$ | $CH_3$ | $R_1$, $R_2$, $R_4$, $R_5$ = H $R_3$ = $CH_3$ | $R_1$, $R_2$, $R_4$, $R_5$ = H $R_3$ = $CH_3$ | M = $(C_2H_5)_3$N $R_1$, $R_2$, $R_4$, $R_5$ = H $R_3$ = $CH_3$ | M = H $R_1$, $R_2$, $R_4$, $R_5$ = H $R_3$ = $CH_3$ | 127–130 | Example 1 |
| 6 | $CH_3$ | $CH_3$ | $R_1$ = $CH_3O$ $R_2$-$R_5$ = H | $R_1$ = $CH_3O$ $R_2$-$R_5$ = H | M = $(C_2H_5)_3$N $R_1$ = $CH_3O$ $R_2$-$R_5$ = H | M = H $R_1$ = $CH_3O$ $R_2$-$R_5$ = H | 86–88 | Example 2 |
| 7 | $CH_3$ | $CH_3$ | $R_1$-$R_4$ = H $R_5$ = F | $R_1$-$R_4$ = H $R_5$ = F | M = $(C_2H_5)_3$N $R_1$-$R_4$ = H $R_5$ = F | M = H $R_1$-$R_4$ = H $R_5$ = F | 94–97 | Example 1 |
| 8 | $CH_3$ | $CH_3$ | $R_2$, $R_3$, $R_4$, $R_5$ = H $R_1$ = $CH_3O$ | $R_2$, $R_3$, $R_4$, $R_5$ = H $R_1$ = $CH_3O$ | M = $(C_2H_5)_3$N $R_1$ = $CH_3O$ | $R_2$, $R_3$, $R_4$, $R_5$, M = H $R_1$ = $CH_3O$ | 101–105 | Example 2 |
| 9 | $CH_3$ | $CH_3$ | $R_1$, $R_2$, $R_5$ = H $R_3$, $R_4$ = Cl | $R_1$, $R_2$, $R_5$ = H $R_3$, $R_4$ = Cl | $R_1$, $R_2$, $R_5$ = H M = $(C_2H_5)_3$N $R_3$, $R_4$ = Cl | $R_1$, $R_2$, $R_5$, M = H $R_3$, $R_4$ = Cl | 115–121 | Example 2 |
| 10 | $CH_3$ | $CH_3$ | $R_1$, $R_2$, $R_4$, $R_5$ = H $R_3$ = F | $R_1$, $R_2$, $R_4$, $R_5$ = H $R_3$ = F | $R_1$, $R_2$, $R_4$, $R_5$ = H M = $(C_2H_5)_3$N $R_3$ = F | $R_1$, $R_2$, $R_4$, $R_5$, M = H $R_3$ = F | 93–95 | Example 1 |
| 11 | $CH_3$ | $CH_3$ | $R_1$, $R_4$, $R_5$ = H $R_2$, $R_3$ = $CH_3O$ | $R_1$, $R_4$, $R_5$ = H $R_2$, $R_3$ = $CH_3O$ | $R_1$, $R_4$, $R_5$ = H M = $(C_2H_5)_3$N $R_2$, $R_3$ = $CH_3O$ | $R_1$, $R_4$, $R_5$, M = H $R_2$, $R_3$ = $CH_3O$ | 112–115 | Example 2 |
| 12 | $CH_3$ | $CH_3$ | $R_1$, $R_2$, $R_4$, $R_5$ = H $R_3$ = Br | $R_1$, $R_2$, $R_4$, $R_5$ = H $R_3$ = Br | $R_1$, $R_2$, $R_4$, $R_5$ = H M = $(C_2H_5)_3$N $R_3$ = Br | $R_1$, $R_2$, $R_4$, $R_5$, M = H $R_3$ = Br | 115–120 | Example 1 |
| 13 | $CH_3$ | $CH_3$ | $R_2$, $R_3$, $R_4$, $R_5$ = H $R_1$ = Br | $R_2$, $R_3$, $R_4$, $R_5$ = H $R_1$ = Br | $R_2$, $R_3$, $R_4$, $R_5$ = H M = $(C_2H_5)_3$N $R_1$ = Br | $R_2$, $R_3$, $R_4$, $R_5$, M = H $R_1$ = Br | 93–97 | Example 1 |
| 14 | $CH_3$ | $CH_3$ | $R_1$, $R_3$, $R_4$, $R_5$ = H $R_2$ = Br | $R_1$, $R_3$, $R_4$, $R_5$ = H $R_2$ = Br | $R_1$, $R_3$, $R_4$, $R_5$ = H M = $(C_2H_5)_3$N $R_2$ = Br | $R_1$, $R_3$, $R_4$, $R_5$, M = H $R_2$ = Br | 104–108 | Example 1 |
| 15 | $CH_3$ | $CH_3$ | $R_1$, $R_2$, $R_3$, $R_4$, $R_5$ = H | $R_1$, $R_2$, $R_3$, $R_4$, $R_5$ = H | $R_1$, $R_2$, $R_3$, $R_4$, $R_5$ = H M = $(C_2H_5)_3$N | $R_1$, $R_2$, $R_3$, $R_4$, $R_5$, M = H | 74–78 | Example 1 |

We claim:

1. A compound selected from those of the formula:

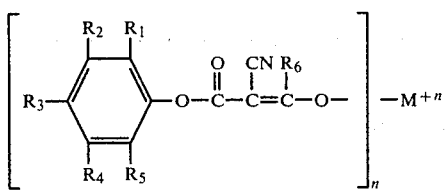

wherein $R_1$, $R_2$, $R_3$, $R_4$ and $R_5$ are each selected from the group comprising hydrogen, halogen, lower alkyl ($C_1$-$C_4$), lower alkoxy ($C_1$-$C_4$), trifluoromethyl and trichloromethyl; $R_6$ is lower alkyl ($C_1$-$C_4$); M is hydrogen or a pharmaceutically acceptable cation; and n is an integer 1, 2, or 3.

2. The compound according to claim 1; 2-cyano-3-hydroxycrotonic acid, p-chlorophenyl ester.

3. The compound according to claim 1; 2-cyano-3-hydroxycrotonic acid, 2,3-dichlorophenyl ester.

4. The compound according to claim 1; 2-cyano-3-hydroxycrotonic acid, o-chlorophenyl ester.

5. The compound according to claim 1; 2-cyano-3-hydroxycrotonic acid, p-methoxyphenyl ester.

6. The compound according to claim 1; 2-cyano-3-hydroxycrotonic acid, p-tolyl ester.

7. The compound according to claim 1; 2-cyano-3-hydroxycrotonic acid, o-methoxyphenyl ester.

8. The compound according to claim 1; 2-cyano-3-hydroxycrotonic acid, o-fluorophenyl ester.

9. The compound according to claim 1; 2-cyano-3-hydroxycrotonic acid, o-methoxyphenyl ester, triethylamine salt.

10. The compound according to claim 1; 2-cyano-3-hydroxycrotonic acid, 3,4-dichlorophenyl ester.

11. The compound according to claim 1; 2-cyano-3-hydroxycrotonic acid, p-fluorophenyl ester.

12. The compound according to claim 1; 2-cyano-3-hydroxycrotonic acid, phenyl ester.

13. The compound according to claim 1; 2-cyano-3-hydroxycrotonic acid, 2,3-dimethoxyphenyl ester.

14. The compound according to claim 1; 2-cyano-3-hydroxycrotonic acid, p-bromophenyl ester.

15. The compound according to claim 1; 2-cyano-3-hydroxycrotonic acid, o-bromophenyl ester.

16. The compound according to claim 1; 2-cyano-3-hydroxycrotonic acid, m-bromophenyl ester.

17. The compound according to claim 1; 2-cyano-3-hydroxycrotonic acid, p-methoxyphenyl ester sodium salt.

18. The compound according to claim 1; 2-cyano-3-hydroxycrotonic acid, p-tolyl ester triethylamine salt.

19. The compound according to claim 1; 2-cyano-3-hydroxycrotonic acid, o-methoxyphenyl ester, cupric salt.

* * * * *